United States Patent

Bean et al.

[11] 4,101,220
[45] Jul. 18, 1978

[54] LASER DOPPLER SPECTROSCOPY WITH SMOOTHENED SPECTRA LINE SHAPES

[75] Inventors: Charles P. Bean; Egidijus E. Uzgiris, both of Schenectady, N.Y.

[73] Assignee: General Electric Company, Schenectady, N.Y.

[21] Appl. No.: 783,186

[22] Filed: Mar. 31, 1977

[51] Int. Cl.² .............................................. G01N 27/26
[52] U.S. Cl. ................................. 356/105; 204/180 R; 204/299 R
[58] Field of Search .................... 356/105; 204/180 R, 204/299 R

[56] References Cited

U.S. PATENT DOCUMENTS 3,984,533  10/1976  Uzgiris ................................... 424/12
4,011,044  3/1977   Uzgiris ............................ 204/299 R

OTHER PUBLICATIONS

Bennett et al., "Laser Doppler Spectroscopy in an Oscillating Electric Field", Phys. Rev. A., vol. 8, No. 5, pp. 2662–2669, 11/73.

Uzgiris, "Laser Doppler Spectrometer for Study of Electrokinetic Phenomena", Rev. Sci. Instrum., vol. 45, No. 1, pp. 74–80, 1/74.

*Primary Examiner*—John K. Corbin
*Assistant Examiner*—Matthew W. Koren
*Attorney, Agent, or Firm*—Nathan D. Herkamp; Joseph T. Cohen; Leo I. MaLossi

[57] ABSTRACT

Changes in electrophoretic mobility distribution of particles in an electric field, as determined by Doppler shifts of laser light scattered by the particles while undergoing oscillation, may be unambiguously measured when the electric field is produced by a frequency modulated square wave voltage. Diminished likelihood of potential ambiguities in the measurement is achieved by smoothing the scattered light spectra and reducing harmonic spectral structures.

10 Claims, 7 Drawing Figures

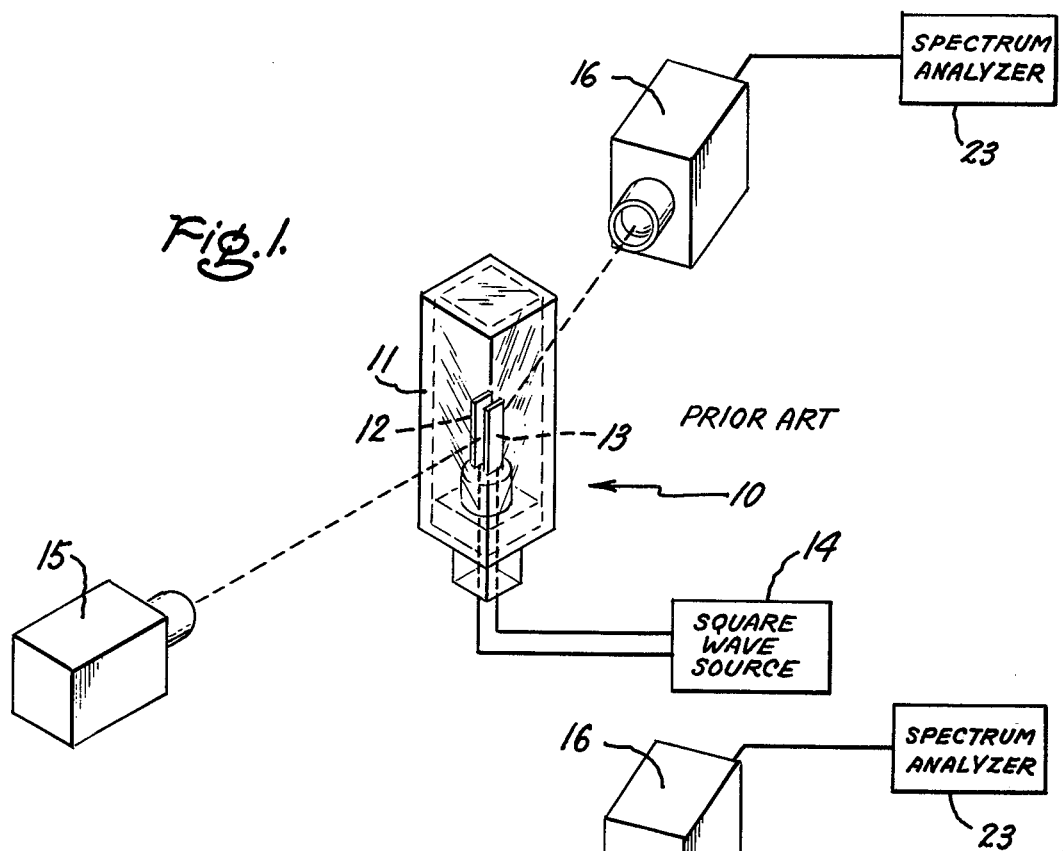
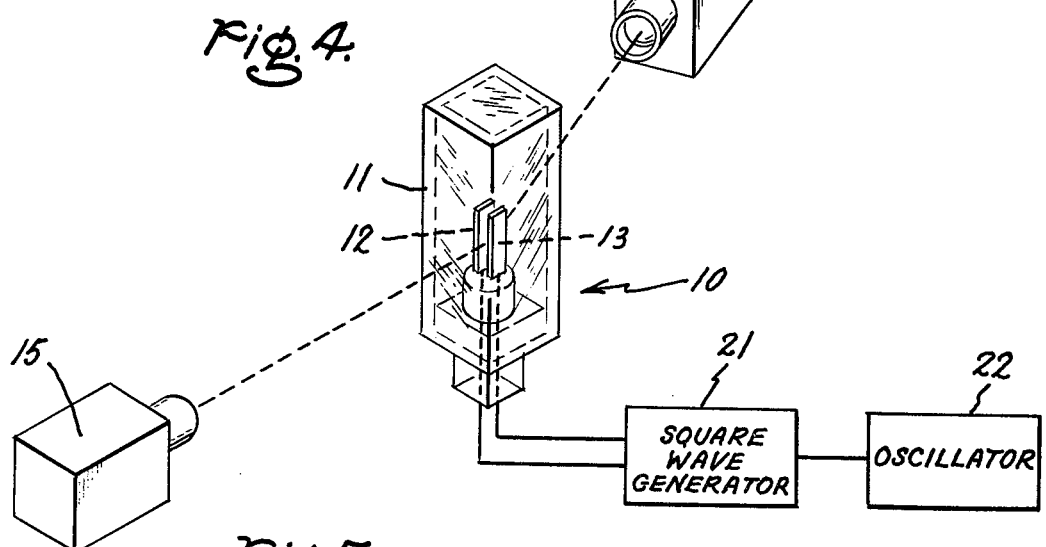
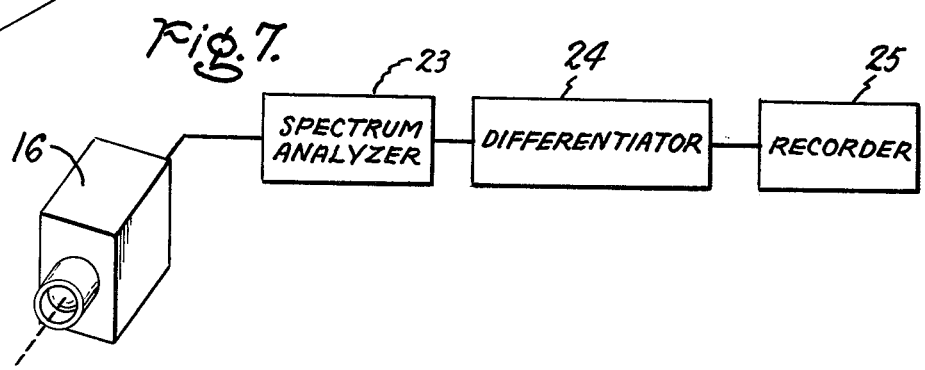

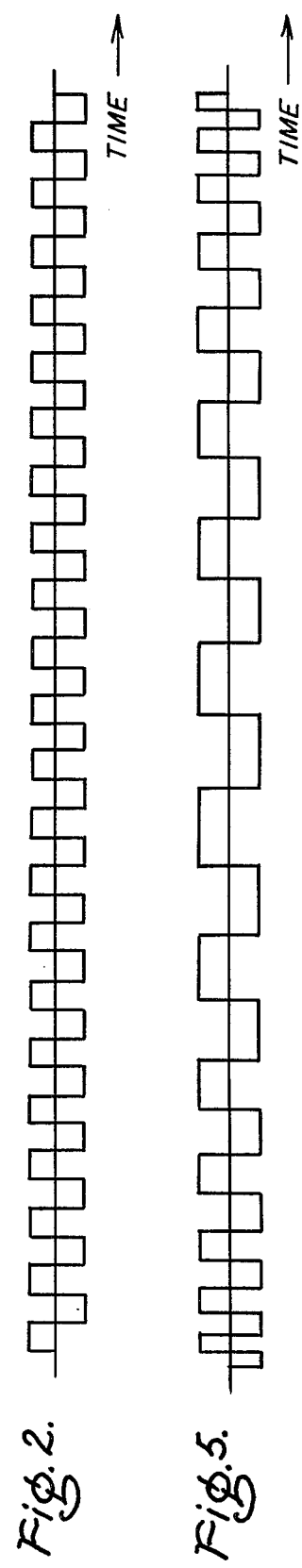

LASER DOPPLER SPECTROSCOPY WITH SMOOTHENED SPECTRA LINE SHAPES

INTRODUCTION

This invention relates to laser Doppler spectroscopy, and more particularly to a method and apparatus for improving information obtained by detecting laser light scattered from oscillating particles suspended in an electric field.

Laser light scattering spectroscopy of particles, including molecules and biological cells, suspended in an electric field, has been shown to be a useful tool for probing electrokinetic phenomena. Specifically, the Doppler shifts of light scattered from these particles are used to measure electrophoretic mobility distributions of the constituents under study. In the case of cells or bioparticles, changes in these mobility distributions have been identified with certain immunological processes.

Conventional laser Doppler spectroscopy involves either pulsing alternating polarity electric fields on and off, or creating the fields with a square wave voltage, since a D.C. field cannot be applied without producing well-known detrimental effects associated with electrode polarization and ion concentration gradients. If pulsing is employed and the pulses are widely separated in time, the result is poor data collecting efficiency, low duty cycle, and necessity for employing electronic sampling techniques in the data collection. On the other hand, if the pulses are close together in time, the square waveform condition is approached. The latter condition causes the detected spectra of the scattered light to break up into harmonics of the square wave frequency. These spectral structures, although completely understood and containing all the necessary information for deconvoluting spectra to mobility distributions, require special deconvolution algorithms which are unwield for multi-component systems. Hence it is conventional practice to use the approximate mobility distributions provided by the envelope of the structures or else to use quite low harmonic frequencies which sometimes cause electrode difficulties and spectra degradation. In view of these impediments to accurate data acquisition, it would clearly be advantageous if the harmonic spectra structure could be broken so that smoother spectra, readily susceptible to umambiguous interpretation, could be obtained. The present invention concerns a method and apparatus for obtaining this result.

Accordingly, one object of the invention is to provide a method and apparatus for obtaining laser Doppler spectroscopy information readily susceptible to unambiguous interpretation.

Another object is to provide a method and apparatus for smoothing scattered light spectra and reducing harmonic spectral structures arising from laser light scattered by particles undergoing oscillatory motion in a square wave electric field.

Another object is to provide a method and apparatus for employing a frequency modulated square wave electric field to control motion of particles undergoing electrophoresis.

Briefly, in accordance with a preferred embodiment of the invention, a method is disclosed for measuring electrophoretic mobility of particles suspended in a fluid and situated in a square wave electric field by heterodyning laser light of a predetermined unshifted frequency with the laser light after undergoing a Doppler shift in frequency caused by the particles scattering laser light impinging thereon, so as to produce a signal representative of the Doppler shift in frequency. The improved method comprises varying the electric field square wave frequency in a predetermined manner.

In accordance with another preferred embodiment of the invention, apparatus for measuring electrophoretic mobility distribution of particles suspended in a fluid comprises a cuvette containing the particles in suspension, a pair of spaced electrodes within the suspension, a source of coherent light directed onto the particles in suspension and onto a wall of the cuvette, photodetecting means positioned to receive light from the coherent source scattered by the particles and by the wall, and a spectrum analyzer coupled to the photodetecting means. A square wave generator is coupled to the electrodes, and means coupled to the square wave generator vary the square wave frequency thereof in a predetermined manner.

BRIEF DESCRIPTION OF THE DRAWINGS

The features of the invention believed to be novel are set forth with particularly in the appended claims. The invention itself, however, both as to organization and method of operation, together with further objects and advantages thereof, may best be understood by reference to the following description taken in conjunction with the accompanying drawings in which:

FIG. 1 is a schematic illustration of apparatus employed in the prior art for detecting changes in electrophoretic mobility of particles in a suspension;

FIG. 2 is a graphical illustration of the output voltage produced by the square wave source of FIG. 1;

FIG. 4 is a schematic illustration of apparatus that may be employed in practicing one embodiment of the invention;

FIG. 5 is a graphical illustration of the output voltage produced by the square wave generator of FIG. 4;

FIG. 7 is a schematic illustration of the readout apparatus that may be employed in practicing another embodiment of the invention.

DESCRIPTION OF TYPICAL EMBODIMENTS

Figure 6:
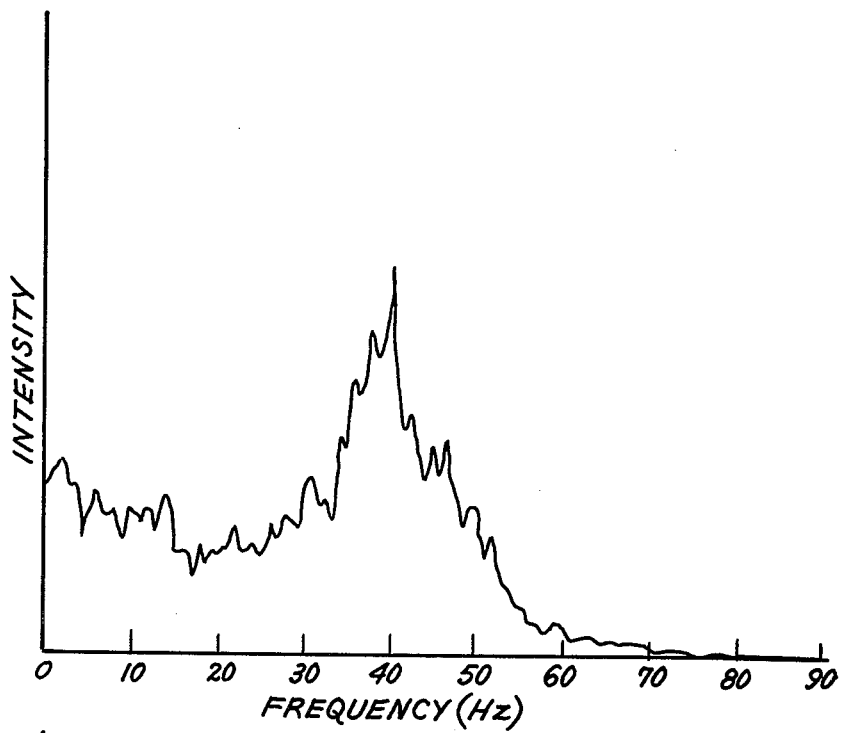
FIG. 6 is an illustration of the Doppler spectra produced for a suspension of human kidney cells using the apparatus of FIG. 4.

FIG. 1 illustrates apparatus such as that described and claimed in E. E. Uzgiris U.S. Pat. No. 3,984,533, issued Oct. 5, 1976 and assigned to the instant assignee, the disclosure thereof being incorporated herein by reference. This apparatus comprises a cuvette 10 including fluid containment means or walls 11 fabricated of a light-transmissive fluid-impenetrable material, such as glass, plastic or the like. A pair of closely-spaced electrodes 12 and 13 are included in cuvette 10. These electrodes are preferably of rectangular shape and have mutually parallel facing surfaces defining an interelectrode gap not exceeding one millimeter in width.

Cuvette 10 is filled with a dilute colloidal suspension containing the microscopic particles to be examined, and a constant frequency square wave electric field is established between electrodes 12 and 13 by square wave source 14. The gap between electrodes 12 and 13 is illuminated by coherent optical energy from a laser 15. The laser may typically be of the helium-neon type operating at 632.8 nanometers. A portion of this energy is scattered by the microscopic particles undergoing examination within the gap between electrodes 12 and 13 and, because of the motion of the scattering particles in the electric field, exhibits a Doppler frequency shift. Energy scattered at a predetermined angle is received by optical detector 16 which is preferably a photomultiplier tube but may be any appropriate square law detector.

Detector 16 receives not only the Doppler-shifted energy scattered by the particles in suspension in the fluid inside container 10, but also receives unshifted energy scattered by fixed scattering objects, such as a wall 11 of container 10. Since detector 16 is a square law detector, its output signal is indicative of the heterodyne product of the two frequencies thus received. To determine the electrophoretic mobility distributions of the particles under study, the output study of detector 16 is typically supplied to a spectrum analyzer 23, such as a Saicor SAI-52A real-time spectrum analyzer. In this fashion, real-time observations of the particle electrophoretic mobility distributions may be obtained with nearly perfect efficiency.

FIG. 2 illustrates the output voltage produced by square wave source 14 in FIG. 1. This square wave is of constant frequency and amplitude and, for a colloidal suspension of human kidney cells in a 0.005 Normal sodium chloride solution may typically produce a spectral curve such as that shown in FIG. 3. As evident from FIG. 3, however, the detected spectra of the scattered light are broken up into harmonics of the square wave frequency. While these spectral structures are thoroughly understood and contain all the necessary information for deconvoluting the spectrum to a mobility distribution, special deconvolution algorithms, which are unwieldy for multicomponent systems, are required for this purpose. Approximate mobility distributions can be obtained from the envelope of the spectra, although knowledge of precise mobility distributions is of greater value.

In analyzing multicomponent systems, quantitative information on partially resolved components may be lost or obscured because of the harmonic structures that result from the square wave nature of the electric field applied to the suspension. Yet if only low harmonic power supply frequencies are employed, spectra degradation is apt to occur, such as electrolysis reactions with resultant gas bubbling and electrode polarization effects.

We have found that modulation of the square wave frequency can substantially reduce the harmonic structures, thereby simplifying analysis and, in some instances, even sharpening the spectra. Accordingly, use of the apparatus of FIG. 4 overcomes the drawbacks associated with spectra of the type shown in FIG. 3. The apparatus of FIG. 4 is identical to that of FIG. 1, with the exception that instead of constant frequency square wave source 14 of FIG. 1, a square wave generator 21, frequency-modulated by the output of an oscillator 22, produces the electric field across electrodes 12 and 13. This field is thus a varying frequency, constant magnitude field corresponding to the output voltage waveform of square wave generator 21, as illustrated in FIG. 5. Generator 21 may typically comprise a Wavetek model 112 square wave generator, which has provision for modulating the frequency of its output waveform manually as well as in accordance with the output voltage of a particular type of oscillator 22, such as a triangular wave generator. A significantly smoother spectrum than that shown in FIG. 3, with equivalent or better resolution, is thereby achieved, as shown in FIG. 6. Hence this technique can be quite useful for analyzing the mobility distributions as a result of, for example, immunological reactions. In the alternative, the frequency of the square wave may be varied at some slow, nonuniform rate, to achieve the same purpose. This type of variation in square wave frequency may readily be achieved by sweeping the frequency of square wave generator 21 up and down manually.

Figure 3:
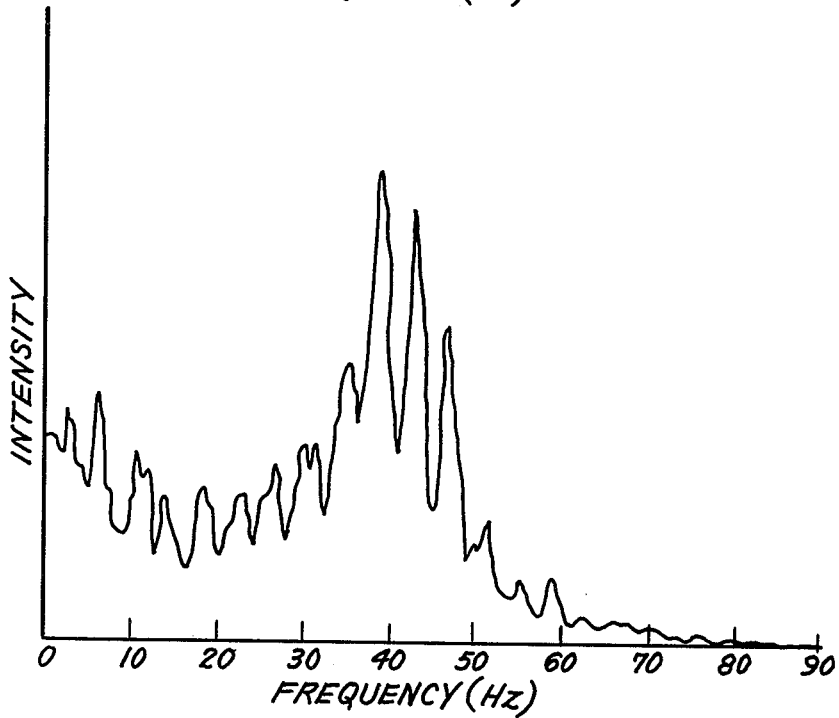
FIG. 3 is an illustration of the Doppler spectra obtained for a suspension of human kidney cells using the apparatus of FIG. 1.

In obtaining the waveform of FIG. 6, the square wave frequency produced by square wave generator 21 is modulated by periodically increasing and decreasing the square wave frequency at linear rates with time. This is accomplished by driving the voltage control input of generator 21 with a relatively slow, triangular voltage wave. The drive frequency, without modulation, may typically be four to five Hz, while the modulation is slow, typically below one Hz. By comparing the spectra of FIGS. 3 and 6, it can be seen that the harmonic peaks in the spectrum of FIG. 3 are substantially reduced, although not completely eliminated. Some structure and shape in the line profile of FIG. 6, which was masked by the harmonics of FIG. 3, is visible as a result of the modulation.

It will be appreciated by those skilled in the art that a randomized period square wave may be a superior approach to fully eliminating harmonic structure in the Doppler spectra. In such case, a constant amplitude bipolar electric field would still be created, but with a stochastic pulse period so that the time average electric field is zero during an averaging time which may typically be on the order of a minute.

It should also be noted that the spectrum smoothed by the apparatus of FIG. 4 readily lends itself to differentiation in order to provide greater sensitivity to minor components of the spectrum. To accomplish this result, the output of photomultiplier 16, as shown in the apparatus of FIG. 4, is connected to spectrum analyzer 23 and then to a differentiator circuit 24, as shown in FIG. 7. Readout is accomplished in a recorder 25 connected to the differentiator, and which, if desired, may be the recorder associated with the spectrum analyzer. Thus portions of the spectrum having a steep slope as a function of frequency, but low amplitude peak, as may be caused by minor components in the suspension undergoing study, are shown as relatively large amplitude components in the output waveform produced by differentiator 24.

The foregoing describes a method and apparatus for obtaining laser Doppler spectroscopy information readily susceptible to unambiguous interpretation. Scattered light spectra are smoothed, and harmonic spectral structures arising from light scattered by particles undergoing oscillatory motion in a square wave electric field are reduced. A frequency modulated square wave electric field controls motion of particles undergoing electrophoresis.

While only certain preferred features of the invention have been shown by way of illustration, many modifications and changes will occur to those skilled in the art. It is, therefore, to be understood that the appended claims are intended to cover all such modifications and changes as fall within the true spirit of the invention.

We claim:

1. In the method of measuring electrophoretic mobility distribution of particles suspended in a fluid and situated in a square wave electric field by heterodyning laser light of a predetermined unshifted frequency with said laser light after undergoing a Doppler shift in frequency caused by said particles scattering laser light impinging thereon so as to produce a signal representative of said Doppler shift in frequency, the improvement comprising varying the electric field square wave frequency in a predetermined manner.

2. The method of claim 1 wherein the step of varying the electric field square wave frequency in a predetermined manner comprises periodically increasing and decreasing said square wave frequency at linear rates with respect to time in accordance with a triangular electrical waveform.

3. The method of claim 2 including the steps of analyzing the power spectrum of said signal representative of said Doppler shift in frequency, and differentiating the analyzed spectrum so as to obtain increased sensitivity to minor components of said spectrum.

4. The method of claim 1 wherein the step of varying the square wave frequency in a predetermined manner comprises varying the square wave frequency stochastically such that the time average electric field within a predetermined averaging period is zero.

5. The method of claim 4 including the steps of analyzing the power spectrum of said signal representative of said Doppler shift in frequency, and differentiating the analyzed spectrum so as to obtain increased sensitivity to minor components of said spectrum.

6. The method of claim 1 including the steps of analyzing the power spectrum of said signal representative of said Doppler shift in frequency, and differentiating the analyzed spectrum so as to obtain increased sensitivity to minor components of said spectrum.

7. Apparatus for measuring electrophoretic mobility distribution of particles suspended in a fluid, comprising:
- a light-transmissive cuvette containing said particles in suspension;
- a pair of spaced electrodes within said suspension;
- a source of coherent light directed through a wall of said cuvette onto said particles in suspension;
- photodetecting means positioned to receive light from said coherent source scattered by said particles and by said wall;
- a spectrum analyzer coupled to said photodetecting means;
- a square wave generator coupled to said electrodes for applying a voltage thereto; and
- means coupled to said square wave generator for varying the square wave frequency thereof in a predetermined manner.

8. The apparatus of claim 7 wherein said means coupled to said square wave generator comprises a triangular wave generator.

9. The apparatus of claim 8 including differentiator means coupled to said spectrum analyzer, and readout means coupled to said differentiator means.

10. The apparatus of claim 7 including differentiator means coupled to said spectrum analyzer, and readout means coupled to said differentiator means.

* * * * *